United States Patent [19]

Larock

[11] 4,288,613

[45] Sep. 8, 1981

[54] CYCLOPENTANONE SYNTHESIS

[75] Inventor: Richard C. Larock, Ames, Iowa

[73] Assignee: Iowa State University Research Foundation, Inc., Ames, Iowa

[21] Appl. No.: 99,321

[22] Filed: Dec. 3, 1979

[51] Int. Cl.³ .................. C07C 69/03; C07C 45/54
[52] U.S. Cl. .......................... 560/231; 568/312; 568/322; 568/323; 568/343; 568/347; 568/348; 568/351; 568/352
[58] Field of Search .......... 260/586 C, 586 R, 429 R; 568/312, 314, 315, 343, 322, 323, 346, 347, 351, 352, 348, 379; 560/231

[56] References Cited

U.S. PATENT DOCUMENTS 4,097,531  6/1978  Bledsoe et al. ................ 260/586 R
4,119,652 10/1978  Knowles et al. ............... 260/429 R

FOREIGN PATENT DOCUMENTS 1258045 12/1971 United Kingdom .
1440372  6/1976 United Kingdom .
1454484 11/1976 United Kingdom .

OTHER PUBLICATIONS

Chemical Abstracts, vol. 78:57872a, (1973).
Ratcliff et al., *J. Org. Chem,* v. 35, pp. 4000-4002, (1970).
Montgomery et al., *J. Am. Chem. Soc.,* v. 89, pp. 6556-6564, (1967).
Sakai et al., *Tetrahedron Letters,* pp. 1287-1290, (1972).
van der Ent et al., *Inorg. Syn.,* v. 14, pp. 92-93, (1973).
Sharpless et al., *J. Am. Chem. Soc.,* v. 97, pp. 5927-5928, (1975).
Lochow et al., *J. Am. Chem. Soc.,* v. 98, pp. 1281-1283, (1976).

*Primary Examiner*—Natalie Trousof
*Assistant Examiner*—Vera C. Clarke
*Attorney, Agent, or Firm*—Zarley, McKee, Thomte, Voorhees & Sease

[57] ABSTRACT

A method of synthesis of cyclopentanones comprising cyclizing a 4-pentenal, preferably under an ethylene atmosphere, in the presence of a catalytically effective amount of a cyclizing, rhodium(I) para-substituted triarylphosphine catalyst.

8 Claims, No Drawings

CYCLOPENTANONE SYNTHESIS

GRANT REFERENCE

The invention described herein was made in the course of work under a grant or award from the Department of Health, Education and Welfare.

BACKGROUND OF THE INVENTION

Prostaglandins are an extremely important biologically active class of $C_{20}$ unsaturated hydroxy acids. They are of widespread occurrence in animal tissues and of varied, extremely potent, biological activities. These acids all have in common the prostanoic acid skeleton, one basic component of which is a five membered cyclopentanone ring.

The therapeutic potential of prostaglandins and the current lack of an abundant natural source of these compounds have led to a number of laboratory investigations to provide a total synthesis as a method of obtaining them. Obviously, a fundamentally important starting material for development of a basic prostaglandin synthesis is the cylopentanone ring, since it is basic to the prostanoic acid skeletal structure.

The cyclization of 4-pentenal to cyclopentanone by chloro tris-(triphenylphosphine) rhodium(I) is known. See for example, Sakai, K.; Ide, J.; Oda, O.; Nakamura, N. *Tetrahedron Lett.* 1972, 1287-1290, and Lochow, C. F.; Miller, R. G. *J. Am. Chem. Soc.* 1976, 98, 1281-1283, which are incorporated herein by reference. However, this reaction has not been achieved at sufficiently high yields to make it an attractive and realistic starting point for prostaglandin synthesis.

In the Sakai et al. reference previously mentioned herein, the catalyst employed in Wilkinson's Catalyst, that is tris(triphenylphosphine) chlororhodium of the formula:

$RhCl(PPh_3)_3$

However, the yield of cyclopentanone from his intramolecular cyclization of 4-pentenal, with Wilkinson's Catalyst is only 17%, and the reaction requires equivalent amounts of the rhodium complex (i.e. it is not catalytic).

It has now been discovered that with the aid of certain newly developed rhodium catalysts, this basic reaction can be conducted under mild conditions to provide high yields of the desired cyclopentanone. This is the primary object of the invention. The method of accomplishing this object, as well as others, will be apparent from the detailed description, which follows.

SUMMARY OF THE INVENTION

Intramolecular cyclization of 4-pentenals to cyclopentanones is significantly improved when it is conducted in the presence of triarylphosphine rhodium complexes, substituted in the para position. Specifically, the preferred catalysts are rhodium(I) chloride tri-p-tolylphosphine, tri-p-anisylphosphine and tris(p-dimethylaminophenyl)phosphine. The yield of the desired cyclopentanone in the present process with the novel catalysts may run from about 75% up to as much as 95%, or even more, using only a catalytic amount of the catalyst.

DETAILED DESCRIPTION OF THE INVENTION 4-pentenals are cyclized to the corresponding cyclopentanones using catalytic amounts of the newly discovered catalyst compounds, in accordance with the following equation:

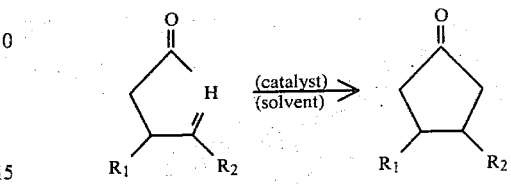

In the above equation $R_1$ and $R_2$ may be hydrogen or substituted or unsubstituted organic moieties, such as alkyl, alkenyl, alkynyl, aryl, acyl, aralkyl, alkoxy, acyloxy, and so forth. Substitution of any moiety in the 3 and 4 positions of the 4-pentenal does not appear to affect the yield of the cyclization reaction at all. Accordingly, any constituents desired may be employed, this not being a limiting feature of the invention. Actual experimentation has shown that the reaction is clearly tolerant to carboxylic acid groups, esters, nitriles, ketones, primary bromides and alcohols. It has, however, been found that if tertiary amines are the substituent $R_1$ and $R_2$ groups, sharply reduced yields are obtained.

Exemplary of the 4-pentenals are those of the formula

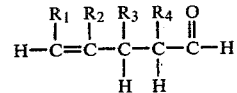

wherein $R_1$, $R_2$, $R_3$ and $R_4$ may be the same or different; $R_1$ and $R_2$ are as defined above; $R_3$ and $R_4$ may be the same as $R_1$ and $R_2$, and may in addition be any other organic moiety.

Additionally, it has been found that the starting pentenal should not be substituted at the 2 and 5 positions. If it is, reaction yields are significantly decreased, and in some cases, non-existent.

In the reported Sakai et al. literature reference, the basic cyclization reaction was conducted in chloroform, benzene and/or $CH_3CN$. It has been found in the present work that the organic solvent employed does not appear to be critical. Generally, any solvent which will dissolve the pentenal and the catalyst and which is otherwise substantially inert, can be used. Examples other than those previously mentioned herein include methylene chloride, tetrahydrofuran, carbon tetrachloride and so forth. From the standpoint of ease of availability and work, methylene chloride has proved to be most satisfactory.

Temperature is a non-limiting factor, and the reaction occurs under mild temperature conditions as well as either at cooler or elevated temperatures. Since it appears to be nonlimiting, it is preferred that ambient temperature conditions be employed.

In prior work with this type of reaction, the amount of 4-pentenal and the rhodium complex, Wilkinson's Catalyst, were equivalent amounts. One of the advantages of the present invention is that lesser than equivalent amounts of the catalyst can be employed; and yet significantly increased product yields are obtained.

In fact, as will be seen from the examples, the amount of catalyst employed may vary from 10% of an equivalent up to an equivalent amount, with no noticeable effect upon yield. That is to say, product yield of the cyclopentanone is just as good at 10% of an equivalent of the catalyst as when using a full equivalent. This is a significant advantage over the prior techniques.

It is preferred that the cyclization reaction of the 4-pentenal occur in the presence of an ethylene atmosphere. As reported in the previously mentioned Lochow reference, the reaction yield is enhanced if the reaction is conducted under an ethylene atmosphere. Thus, from the standpoint of practicality this is the preferred way of conducting the reaction; although it should be understood that it can be conducted without employing an ethylene atmosphere if desired.

The three new catalyst compounds found to be highly useful in converting the 1-al-4-ene system into cyclopentanones at high yields, even when catalytic amounts are employed, are all triarylphosphines substituted in the para position. These compounds are: chloro rhodium(I) (tri-p-tolylphosphine); chloro rhodium (I) (tri-p-anisylphosphine); and chloro rhodium (I) tris-(p-dimethylaminophenyl) phosphine. It is believed other halo rhodium salts such as the corresponding bromo- and iodo-salts would also work. The highest yield of cyclopentanone is obtained using two equivalents of ligand per rhodium and this is therefore preferred. However, at times, particularly if the phosphine is old or impure, up to three equivalents of phosphine ligand moiety may be used.

The rhodium complex catalysts of this invention, just previously mentioned, are most conveniently prepared in situ by the addition of the desired ligand to a solution of chlorobis (cyclooctene)rhodium (I) dimer in methylene chloride under ethylene according to the following equation:

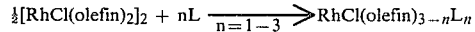

The chlorobis (cyclooctene)rhodium(I) dimer is readily prepared according to van der Ent, A.; Onderdelineker, A. L.; *Inorg. Syn.*, 1973, 14, 92–93 which is incorporated herein by reference. One can also use the chloro bis (ethylene)rhodium(I) complex as well and it is commercially available from Strem. As can be seen, this procedure allows one to vary the ratio of the desired ligand to the rhodium so as to optimize the yield of the cyclopentanone. Again, as has been previously mentioned, the number of ligands per rhodium being 2:1 is most preferred.

As heretofore mentioned, the cyclization of substituted 4-pentenals with the specific three catalysts employed in this invention appear to be equally effective at concentrations as low as 10% of equivalency as when equivalent amounts are used. However, it has been noted in experimenting that yields drop off drastically when only 1% of the catalyst is employed.

As will be seen from the examples which follow, a large variety of cyclopentanones can be prepared by the rhodium catalyzed cyclizations. The reaction affords a very valuable new method for the synthesis of cyclopentanones, useful in prostaglandin synthesis.

However, it should be noted that the reaction does not appear applicable to the formation of cyclic ketones of other ring sizes than the five membered ring.

Additional features worthy of specific mention relate to substitution of other organic groups on the 4-pentenal, and correspondingly on the cyclopentanone ring. The reaction appears to be extremely tolerant to a variety of groups on the 3 or 4 position. This again is evidenced by the examples.

In the examples which will follow hereinafter, certain generalized procedures were employed, in each reaction.

All reagents were used directly as obtained commercially unless otherwise noted. The solvents were dried over molecular sieves, distilled and degassed before use. All infrared spectra were obtained on a Beckman IR 4250 spectrophotometer. $^1$H NMR spectra were obtained on Varian A-60 and HA-100 instruments and the $^{13}$C NMR spectra on a JOEL FX 90 Q. A Varian 920 gas chromatograph with a thermal conductivity detector was used for most GLPC analyses, more difficult separations being determined on a Varian 3700 gas chromatograph. Mass spectra were recorded on an AEI MS 902 and a Finnegan 4023 GC/MS combination.

The triarylphosphine ligands were used as obtained commercially from Strem, of Newburyport, Massachusetts, that is the following ligand structures: Tri-p-anisylphosphine, tri-p-tolylphosphine, tris(p-dimethylaminophenyl) phosphine.

The 4-pentenal starting material was prepared by three different procedures. Collins oxidation of 4-penten-1-ol gave a 44% yield of 4-pentenal. This was in accordance with the procedure of Ratcliff, R.; Rodehorst, R. *J. Org. Chem.* 1970, 35, 4000–4002 which is incorporated by reference. The procedure of Sharpless and Akashi (Sharpless, K. B.; Akashi, *K. J. Am. Chem. Soc.*) 1975, 97, 5927–5928, which is incorporated by reference, afforded a 41% yield of the aldehyde. The low yields were due mainly to high water solubility of the product. The majority of the 4-pentenal starting material was prepared by Claisen rearrangement of allyl vinyl ether, obtained from Columbia Organic Chemicals, in accordance with Montgomery, L. K.; Matt, J. W. *J. Am. Chem. Soc.* 1967, 89, 6556–6564, which is incorporated herein by reference. In this procedure 4-pentenal was obtained in a 65% yield having a boiling point of 102°–103° C. Other substituted pentenals were obtained using conventional literature reported procedures.

The following is a typical procedure used when the cyclization reaction is run under ethylene, the most preferred embodiment. In a 25 ml. round bottom flask equipped with a septum inlet tube were placed the rhodium complex and an appropriate amount of phosphine. The methylene chloride solution (5 ml.) containing the aldehyde (1.0 mmol), was added by syringe and the flask flushed with argon and cooled with liquid nitrogen. Ethylene was then admitted into the flask until a distinct layer of liquid ethylene was present on the frozen methylene chloride. The flask was allowed to warm to room temperature with the excess ethylene escaping through a mercury bubbler. After warming to room temperature, the flask was sealed. The determination of yields by gas chromatography was carried out. It also has additionally been found satisfactory to simply bubble ethylene through the reaction system.

EXAMPLES 1–3

In accordance with Table 1 set forth below, the three catalysts specifically heretofore mentioned were utilized at a 50% of equivalent amount to cyclize 4-pentenal, in the presence of an ethylene atmosphere, utilizing saturated methylene chloride solvent. As can be seen from the table, the percentage of desired cyclopentanone product varied with the number of equivalents of ligand per rhodium. The best results appeared when two equivalents per rhodium atom were employed.

TABLE I

| Ligand | % Yield of Cyclopentanone Equivalents of Phosphine Ligand:Rhodium | | |
|---|---|---|---|
| | 1 | 2 | 3 |
| P(−C₆H₄−N(CH₃)₂)₃ | 41 | 90 | 95 |
| P(−C₆H₄−CH₃)₃ | 65 | 97 | 72 |

TABLE I-continued

| Ligand | % Yield of Cyclopentanone Equivalents of Phosphine Ligand:Rhodium | | |
|---|---|---|---|
| | 1 | 2 | 3 |
| P(−C₆H₄−OCH₃)₃ | 70 | 98 | 88 |

EXAMPLES 4–27

Generality of the reaction for use with 4-pentenal and substituted 4-pentenals (variations of $R_1$ and $R_2$ at the 3,4 positions as previously discussed), as well as other substituents, as demonstrated by the following examples:

TABLE II

RHODIUM CATALYZED CYCLIZATION OF UNSATURATED ALDEHYDES[a]

| EXAMPLE | ALDEHYDE | LIGAND[b] | % CATALYST[c] | PRODUCT | % YIELD[d] |
|---|---|---|---|---|---|
| 4 | ⟶CHO (4-pentenal) | P(−C₆H₄−CH₃)₃ | 50 | cyclopentanone | 97 |
| 5 | | | 10 | | 95 |
| 6 | | | 1 | | 20 |
| 7 | | P(−C₆H₄−OCH₃)₃ | 50 | | 98 |
| 8 | | | 10 | | 88 |
| 9 | | P(−C₆H₄−N(CH₃)₂)₃ | 50 | | 90 |
| 10 | | | 20 | | 78 |
| 11 | | | 10 | | 90 |
| 12 | | | 1 | | 10 |
| 13 | 3-methyl-4-pentenal CHO | P(−C₆H₄−CH₃)₃ | 50 | 2-methylcyclopentanone | 51 |
| 14 | | | 10 | | 24 |
| 15 | | P(−C₆H₄−OCH₃)₃ | 50 | | 53 |
| 16 | | | 10 | | 37 |
| 17 | 4-methyl-4-pentenal CHO | P(−C₆H₄−CH₃)₃ | 50 | 3-methylcyclopentanone | 90 |
| 18 | | P(−C₆H₄−OCH₃)₃ | 50 | | 95 |
| 19 | | P(−C₆H₄−N(CH₃)₂)₃ | 50 | | 98 |
| 20 | hex-3-enal CHO | P(−C₆H₄−CH₃)₃ | 50 | 2-methylcyclopentanone | 59 |
| 21 | | | 10 | | 34 |
| 22 | | P(−C₆H₄−OCH₃)₃ | 50 | | 52 |
| 23 | cyclohexyl vinyl CHO | | 10 | spiro ketone | 40 |
| 24 | | P(−C₆H₄−N(CH₃)₂)₃ | 10 | | 93 |
| 25 | methylenecyclohexyl CHO | P(−C₆H₄−N(CH₃)₂)₃ | 50 | bicyclic ketone cis/trans = 64/36 | 90 |

TABLE II-continued

RHODIUM CATALYZED CYCLIZATION OF UNSATURATED ALDEHYDES[a]

| EXAMPLE | ALDEHYDE | LIGAND[b] | % CATALYST[c] | PRODUCT | % YIELD[d] |
|---|---|---|---|---|---|
| 26 | (cyclohexyl with CHO and vinyl) cis/trans = 36/64 | $P(-C_6H_4-N(CH_3)_2)_3$ | 50 | (bicyclic ketone) cis/trans = 27/73 | 89 |
| 27 | (pentenal) CHO | $P(-C_6H_5)_3$ | 50 | 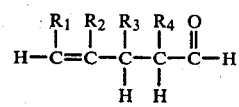 | 19 |
|  |  | $P(-C_6H_4-OCH_3)_3$ | 20 |  | 19 |

[a] Chlorobis(cyclooctene)rhodium(I) dimer at room temperature in methylene chloride saturated with ethylene.
[b] Two equiv. per rhodium.
[c] Mole % rhodium per aldehyde.
[d] GLPC yields using an internal standard; isolated yields underlined.

It therefore can be seen that a significant number of cyclopentanone ring compounds can be prepared by varying the amount of catalyst down to as low as 10% and with a variety of alkyl substituents as well as functional groups not seeming to affect the reaction product significantly.

What is claimed is:

1. A method of synthesis of cyclopentanones comprising: cyclizing a 4-pentenal in the presence of a catalytically effective amount of a cyclizing halo rhodium parasubstituted triarylphosphine catalyst and in the presence of a suitable organic solvent for said pentenal and catalyst.

2. The process of claim 1 wherein said process is conducted in an ethylene atmosphere.

3. The process of claim 1 wherein said catalyst is selected from the group consisting of rhodium halide tri-p-tolylphosphine, rhodium halide tri-p-anisylphosphine and rhodium halide tris(p-dimethylaminophenyl)-phosphine.

4. The process of claim 3 where two equivalents of ligand per rhodium are employed.

5. The process of claim 4 wherein the amount of said catalyst is from 10% of an equivalent amount up to a full equivalent.

6. The process of claim 1 wherein said process is conducted in the presence of a substantially inert organic solvent for said pentenal.

7. The process of claim 1 wherein said pentenal has the general formula of $$H-\underset{\underset{}{}}{C}=\underset{\underset{}{}}{C}-\underset{\underset{H}{|}}{\overset{R_1}{C}}-\underset{\underset{H}{|}}{\overset{R_2}{C}}-\underset{}{\overset{R_3}{C}}-\underset{}{\overset{R_4}{C}}-\overset{O}{\overset{\|}{C}}-H$$

wherein $R_1$, $R_2$, $R_3$ and $R_4$ may be the same or different, and $R_1$ and $R_2$ are selected from the group consisting of hydrogen, and unsubstituted alkyl, alkenyl, alkynyl, aryl, aralkyl, alkoxy and acyloxy groups, and wherein $R_3$ and $R_4$ may be the same as $R_1$ and $R_2$, and may in addition be any other organic moiety.

8. The process of claim 7 wherein $R_1$ and $R_4$ are hydrogen.

* * * * *